US012564390B2

(12) United States Patent
Wernersson et al.

(10) Patent No.: US 12,564,390 B2
(45) Date of Patent: Mar. 3, 2026

(54) BIOPSY ARRANGEMENT

(71) Applicant: NeoNavia AB, Vallentuna (SE)

(72) Inventors: Ola Wernersson, Halmstad (SE);
Magnus Olsen, Vallentuna (SE);
Kai-Uwe Schässburger, Hamburg (DE)

(73) Assignee: NEONAVIA AB, Vallentuna (SE)

( * ) Notice: Subject to any disclaimer, the term of this patent is extended or adjusted under 35 U.S.C. 154(b) by 971 days.

(21) Appl. No.: 17/642,601

(22) PCT Filed: Sep. 3, 2020

(86) PCT No.: PCT/EP2020/074530
§ 371 (c)(1),
(2) Date: Mar. 11, 2022

(87) PCT Pub. No.: WO2021/047984
PCT Pub. Date: Mar. 18, 2021

(65) Prior Publication Data
US 2022/0338850 A1     Oct. 27, 2022

(30) Foreign Application Priority Data
Sep. 12, 2019     (EP) ..................................... 19196876

(51) Int. Cl.
*A61B 10/02*          (2006.01)
(52) U.S. Cl.
CPC .. *A61B 10/0275* (2013.01); *A61B 2010/0208* (2013.01)
(58) Field of Classification Search
CPC .............. A61B 2010/0208; A61B 10/02–0291
See application file for complete search history.

(56) References Cited

U.S. PATENT DOCUMENTS

| | | | |
|---|---|---|---|
| 5,121,751 A | 6/1992 | Panalletta | |
| 5,188,118 A | 2/1993 | Terwilliger | |
| | (Continued) | | |

FOREIGN PATENT DOCUMENTS

| | | |
|---|---|---|
| DE | 20211934 U1 | 9/2002 |
| EP | 1832234 A2 | 9/2007 |
| | (Continued) | |

OTHER PUBLICATIONS

International Search Report for related International Application No. PCT/EP2020/074530 mailed Oct. 22, 2020.

*Primary Examiner* — Tse W Chen
*Assistant Examiner* — Evelyn Grace Park
(74) *Attorney, Agent, or Firm* — Renner, Otto, Boisselle & Sklar, LLP

(57) ABSTRACT

A biopsy arrangement for taking a biopsy in a human or animal tissue, said biopsy arrangement comprising: —a needle arrangement (3) comprising an elongated inner needle part (5) and an elongated outer needle part (7), which outer needle part (7) is a hollow member in which the inner needle part (5) fits coaxially, wherein the two needle parts can be provided in at least two different positions in relation to each other; —an activator (11) which is arranged in the biopsy arrangement (1) such that it can be moved within the biopsy arrangement, said activator (11) comprising: —a first activating part (13) which is configured to control a needle locking device (21) provided in the biopsy arrangement (1) to lock or not lock the inner needle part (5) and the outer needle part (7) to each other; and —a second activating part (15) which is configured to control a needle translation device (31) provided in the biopsy arrangement (1) to change a position of the inner (5) and outer needle parts (7) in relation to each other, said needle translation device (31) being connected to at least one of the inner or outer needle parts (5, 7), whereby a movement of the activator (11) within (Continued)

the biopsy arrangement (1) can affect a position of both the first and the second activating parts (13, 15) whereby both the needle locking device (21) and the needle translation device (31) can be controlled.

9 Claims, 6 Drawing Sheets

(56) References Cited

U.S. PATENT DOCUMENTS

| 5,348,022 | A | 9/1994 | Leigh et al. |
| 5,392,790 | A | 2/1995 | Kanner et al. |
| 5,615,690 | A | 4/1997 | Giurtino et al. |
| 6,120,463 | A | 9/2000 | Bauer |
| 7,828,748 | B2 | 11/2010 | Hibner |
| 8,282,573 | B2 | 10/2012 | Shabaz et al. |
| 8,313,444 | B2 | 11/2012 | Thompson et al. |

| 2004/0171989 | A1* | 9/2004 | Horner ............. A61M 25/0618 |
| | | | 604/164.08 |
| 2009/0012423 | A1 | 1/2009 | Peters |
| 2012/0029354 | A1 | 2/2012 | Mark et al. |
| 2014/0336531 | A1 | 11/2014 | Fiebig et al. |
| 2021/0128122 | A1* | 5/2021 | Stoianovici ........ A61B 10/0275 |

FOREIGN PATENT DOCUMENTS

| EP | 2323563 | B1 | 2/2012 |
| EP | 2520237 | A1 | 11/2012 |
| EP | 3206587 | A1 | 8/2017 |
| RU | 2212848 | C2 | 9/2003 |
| WO | 2000010465 | A1 | 3/2000 |
| WO | 2000056220 | A1 | 9/2000 |
| WO | 2008115526 | A2 | 9/2008 |
| WO | 2012015801 | A1 | 2/2012 |
| WO | 2014007380 | A1 | 1/2014 |
| WO | 2016058845 | A1 | 4/2016 |

* cited by examiner

BIOPSY ARRANGEMENT

This application is a national phase of International Application No. PCT/EP2020/074530 filed Sep. 3, 2020, which claims priority to European Patent Application No. 19196876.7 filed Sep. 12, 2019, the entire disclosures of which are hereby incorporated by reference.

TECHNICAL FIELD OF THE INVENTION

The present invention relates to a biopsy arrangement for taking a biopsy in a human or animal tissue.

BACKGROUND

Today it is generally accepted that the final diagnosis of malignant suspicious lesions has to be confirmed using biopsy techniques. The most commonly performed cell- and tissue-sampling techniques are fine needle aspiration (FNA) using mainly 22 G and 23 G needles (0.6-0.7 mm in diameter) and core needle biopsy (CNB) or vacuum assisted biopsy (VAB) needles using everything between 8 G and 18 G needles (1.3-4.2 mm in diameter), with the latter two techniques dominating globally. Because of the significantly improved sensitivity and minimally invasiveness when combining needle biopsy techniques with imaging guidance the number of open surgical biopsies is steadily declining.

In contrast to FNA, CNB and VAB allow for large volume tissue sampling which permits differentiation between in situ and invasive lesions, histologic diagnosis of micro-calcifications and the analysis of several relevant biomarkers.

There are significant advancements when it comes to visualization techniques continuously pushing the boundaries for what is possible when it comes to locating a suspicious lesion. In addition a number of developments like the use of advanced biomarkers for following and personalizing adjuvant treatment are defining new requirements concerning very precise and minimally invasive tissue sampling.

The distal end of biopsy needles used in most CNB and VAB devices is a sharp, solid tip, which is needed for penetration of tissue towards the location where a biopsy is to be taken. To penetrate suspicious lesions the needle has to be inserted manually or using the generally used spring-loaded mechanism to thrust the needle into the lesions with a predetermined length. Thereafter a tissue sampling procedure is initiated, usually incorporating the opening of a residual space which is filled with surrounding tissue and subsequently closed, whereby the tissue inside the residual space is severed from surrounding tissue.

The opening and possible closing of the residual space is usually accomplished by the relative movement of two separate elements of the needle biopsy assembly, e.g. an inner sampling needle relative to an outer cutting needle, an inner trocar relative to an outer sampling needle, or a distal cutting blade relative to a distal tip sampling needle.

Different types of biopsy devices are well known in the art. A few documents describing biopsy devices with hollow needles and elongated rods are WO 0056220, EP 2520237, US 2012/0029354, U.S. Pat. Nos. 5,188,118, 5,348,022, 5,121,751, 6,120,463, 8,282,573, 7,828,748, WO 2014/007380, DE 20211934U, U.S. Pat. Nos. 8,313,444, and 5,392,790. A core biopsy arrangement has been described by the present applicant in EP 2323563, wherein a reciprocating longitudinal movement is applied to a biopsy needle. In EP 3206587 and WO 2016/058845 the present applicant discloses a biopsy arrangement utilizing such a reciprocating longitudinal movement of the biopsy needle where specific details around the needle configuration comprising an inner trocar and a specific configuration of the needle distal tip for cutting the sample is described. Further, the following documents describe biopsy arrangements comprising blades or severing arrangements: WO 2012015801, EP 1832234, WO 0010465, U.S. Pat. No. 5,615,690, RU 2212848, US 2009012423, WO 2008115526.

Additionally, the manual insertion of large diameter needles through healthy tissue towards the targeted lesion can be cumbersome, especially if said tissue is dense or fibrotic. The physician has to apply manual force to navigate the sharp needle towards the lesion while maintaining dexterity and control not to injure vessels and organs. The insertion process is a source of patient anxiety and should therefore be as short and efficient as possible.

SUMMARY

An object of the invention is to provide an improved biopsy arrangement.

This is achieved by a biopsy arrangement according to claim 1.

According to one aspect of the invention a biopsy arrangement for taking a biopsy in a human or animal tissue is provided, said biopsy arrangement comprising:

a needle arrangement comprising an elongated inner needle part and an elongated outer needle part, which outer needle part is a hollow member in which the inner needle part fits coaxially, wherein the two needle parts can be provided in at least two different positions in relation to each other;

an activator which is arranged in the biopsy arrangement such that it can be moved within the biopsy arrangement, said activator comprising:

a first activating part which is configured to control a needle locking device provided in the biopsy arrangement to lock or not lock the inner needle part and the outer needle part to each other; and a second activating part which is configured to control a needle translation device provided in the biopsy arrangement to change a position of the inner and outer needle parts in relation to each other, said needle translation device being connected to at least one of the inner or outer needle parts, whereby a movement of the activator within the biopsy arrangement can affect a position of both the first and the second activating parts whereby both the needle locking device and the needle translation device can be controlled.

Hereby a biopsy arrangement is provided which can lock the inner and outer needle parts together for example during insertion of the needle arrangement to the sampling position and then release said locking of the needle parts for the sampling procedure. An activator is provided in the biopsy arrangement and according to the invention a movement of the activator can both affect the locking or releasing of the needle parts to each other and affect the position of the needle parts to each other, i.e. perform a sampling procedure. Hereby the needle parts can suitably be kept locked together during insertion to a sample position and the activator is moved in order to first release the lock between the needle parts and then change a position of the inner and outer needle parts in relation to each other in order to take a sample. For example, in a so called core needle biopsy the outer needle part is first retracted and the inner needle part comprises a sample receiving recess which then is filled and the sample in the sample receiving recess is then cut from the tissue when the outer needle part is moving forward again. The possibility to perform these steps by just moving the activator is advantageous. Hereby it is possible to for example just move the actuator linearly and hereby by one single linear movement perform both release of needle lock and sampling. Hereby, thanks to the single linear movement, a simple and effective electromechanical control can be provided for controlling the sampling. Hereby a biopsy arrangement which can be easily handled by the user can be provided. Furthermore the possibility to lock the needle parts together is suitable during positioning of the needle and reciprocating pulses can be provided to the locked needle arrangement which is advantageous for needle insertion and positioning. Furthermore the moving of the activator can easily be performed by a motor and the moving of the activator can easily be controlled in different steps allowing a user to control the sampling process. With a biopsy arrangement according to the invention the needle can be inserted into a correct position in a locked state and possibly with added reciprocating pulses. The position can be adjusted and validated and then the sampling procedure is performed. Hereby the chance of achieving a large and representative sample is improved.

In one embodiment of the invention the biopsy arrangement further comprises a release device which is configured to release a connection between the second activating part of the activator and the needle translation device when the activator has been moved to a certain position, whereby a movement of the activator within the biopsy arrangement can control at least three different functions comprising the control of the needle locking device to lock or not lock the inner needle part and the outer needle part to each other, the control of the position of the inner and outer needle parts in relation to each other and the release of the connection between the second activating part and the needle translation device.

In one embodiment of the invention the activator is arranged within the biopsy arrangement such that it can be moved linearly in one direction within the biopsy arrangement in order to control the at least three different functions. Hereby it is possible to by one single linear movement perform both release of needle lock and sampling. Thanks to the single linear movement, a simple and effective electromechanical control can be provided for controlling the sampling. Hereby a biopsy arrangement which can be easily handled by the user can be provided.

In one embodiment of the invention said needle translation device comprises a resilient element which will strive to return the inner or outer needle part if it has been moved, back to an original position.

In one embodiment of the invention the release device is positioned within the biopsy arrangement such that it will release the connection between the second activating part and the needle translation device when the needle translation device has been moved within the biopsy arrangement by the second activating part a certain distance and hereby the resilient element has been loaded and will be released when the needle translation device is released from the second activating part.

In one embodiment of the invention said inner needle part comprises a sample receiving recess along a part of its length, wherein said outer needle part can be provided in at least a first outer needle part position where the outer needle part is covering the sample receiving recess and a second outer needle position where the outer needle part is retracted and is not covering the sample receiving recess which is open for receiving a sample.

In one embodiment of the invention the needle translation device comprises an outer needle connection member connected to the outer needle part, whereby a translation of the needle translation device is transferred to a translation of the outer needle part.

In one embodiment of the invention said needle locking device can be provided in at least a first needle locking device state and a second needle locking device state, where the needle locking device in said first needle locking device state is locking the inner needle part and the outer needle part to each other such that they cannot be moved in relation to each other and in said second needle locking device state the needle locking device is not locking the inner needle part and the outer needle part to each other, whereby the first activating part can affect the state of the needle locking device by movement of the activator.

In one embodiment of the invention said activator is configured such that it can be connected to a motor such that the position of the activator can be controlled by the motor.

In one embodiment of the invention the biopsy arrangement further comprises a pulsing device which is configured to interact with the needle arrangement such that reciprocating pulses of the pulsing device can be transferred to the needle arrangement. Reciprocating pulses provided to the locked needle arrangement during insertion is advantageous for needle insertion and positioning. The needle can be inserted into a correct position in a locked state and with added reciprocating pulses. The position can be adjusted and validated and then the sampling procedure is performed.

In one embodiment of the invention the biopsy arrangement further comprises an activator moving device configured for engaging with the activator and transferring a movement to the activator.

In one embodiment of the invention the biopsy arrangement comprises a reusable driver unit and a single use probe, wherein said single use probe comprises said needle arrangement, said needle locking device, said needle translation device and said activator and said driver unit comprises an activator moving device configured for engaging with the activator and transferring a movement to the activator.

In one embodiment of the invention the driver unit further comprises the pulsing device.

BRIEF DESCRIPTION OF THE DRAWINGS

FIG. 5a is a side view of a biopsy arrangement according to one embodiment of the invention.

FIG. 5b is a cross section of the biopsy arrangement as shown in FIG. 5a.

DETAILED DESCRIPTION OF EMBODIMENTS

Figure 3:
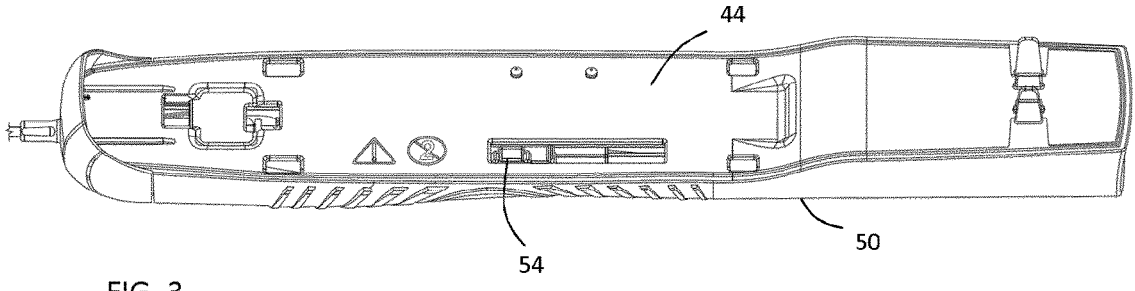
FIG. 3 is a perspective view from above of a probe of a biopsy arrangement according to one embodiment of the invention.
Figure 4:
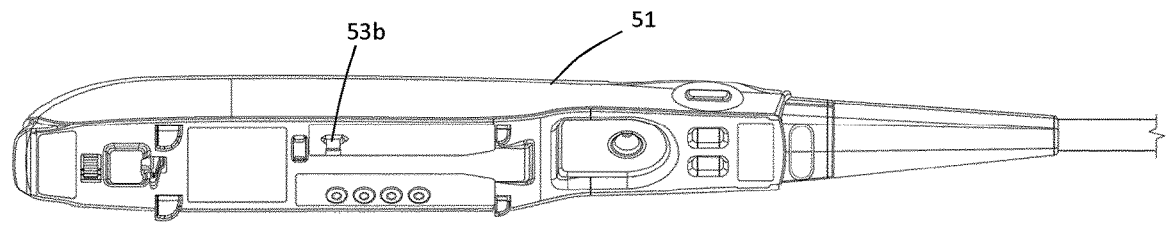
FIG. 4 is a perspective view of a driver unit of a biopsy arrangement according to one embodiment of the invention.
Figures 5A, 5B:
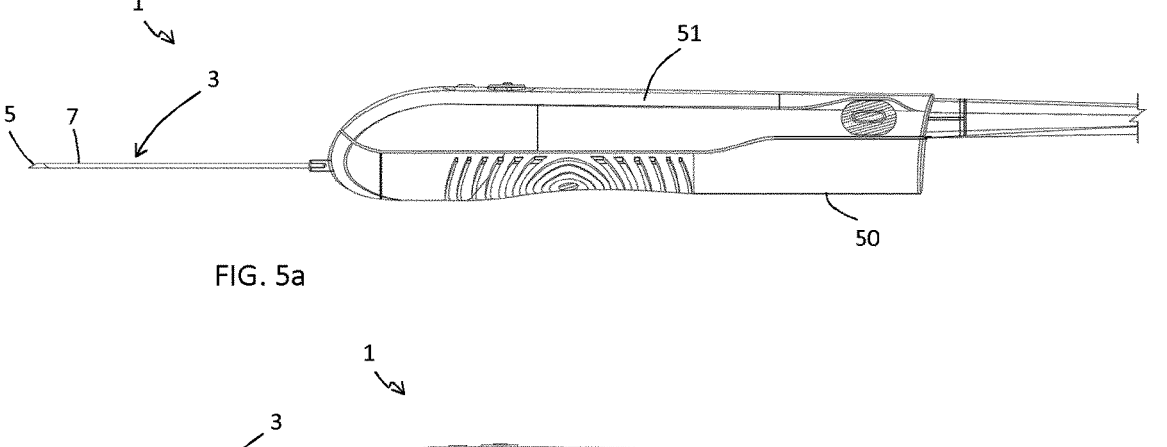

FIGS. 1a-1d show the inside of a probe 50 of a biopsy arrangement 1 according to one embodiment of the invention in four different sampling positions. In this embodiment of the invention the biopsy arrangement 1 comprises a reusable driver unit 51 and a single use probe 50 which are connected during sampling. The single use probe 50 is shown in a perspective view in FIG. 3 and the driver unit is shown in a perspective view in FIG. 4 and the two parts are shown assembled in FIG. 5*a*. However in another embodiment of the invention the biopsy arrangement 1 does not have to be separated into a single use probe and a reusable driver but could instead be one single unit. In FIGS. 1*a*-1*d* a cover plate 44 has been removed and some of the inner parts of the biopsy arrangement 1 can be seen.

A biopsy arrangement 1 for taking a biopsy in a human or animal tissue is provided according to the invention. Said biopsy arrangement 1 comprises a needle arrangement 3. The needle arrangement 3 can be seen in FIGS. 5*a* and 5*b* and it comprises an elongated inner needle part 5 and an elongated outer needle part 7, which outer needle part 7 is a hollow member in which the inner needle part 5 fits coaxially. The two needle parts 5, 7 can be provided in at least two different positions in relation to each other. In some embodiments of the invention, but not necessarily, the inner needle part 5 comprises a sample receiving recess 6 along a part of its length, i.e. a side aperture for receiving sample. The outer needle part 7 and the inner needle part 5 are movable in relation to each other such that the outer needle part 7 is covering the sample receiving recess 6 in a first needle position and the outer needle part 7 is not covering the sample receiving recess 6 in a second needle position. In the embodiment as shown in FIGS. 1-7 the outer needle part 7 is moved, i.e. retracted for opening the sample receiving recess 6 and forwarded again for severing the sample within the sample receiving recess. However, in another embodiment the inner needle part 5 is instead moved.

Figures 1A, 1B:
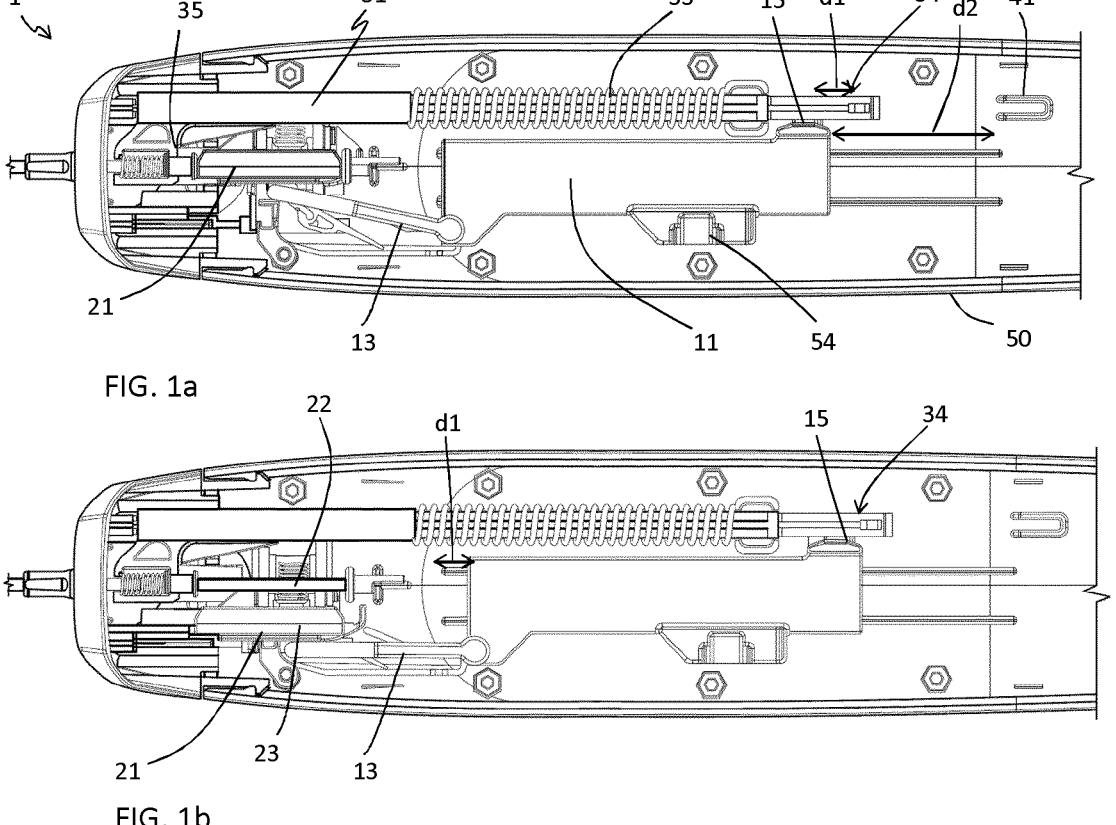
FIGS. 1a-1d show the inside of a probe of a biopsy arrangement according to one embodiment of the invention in four different sampling positions.
Figures 1C, 1D:
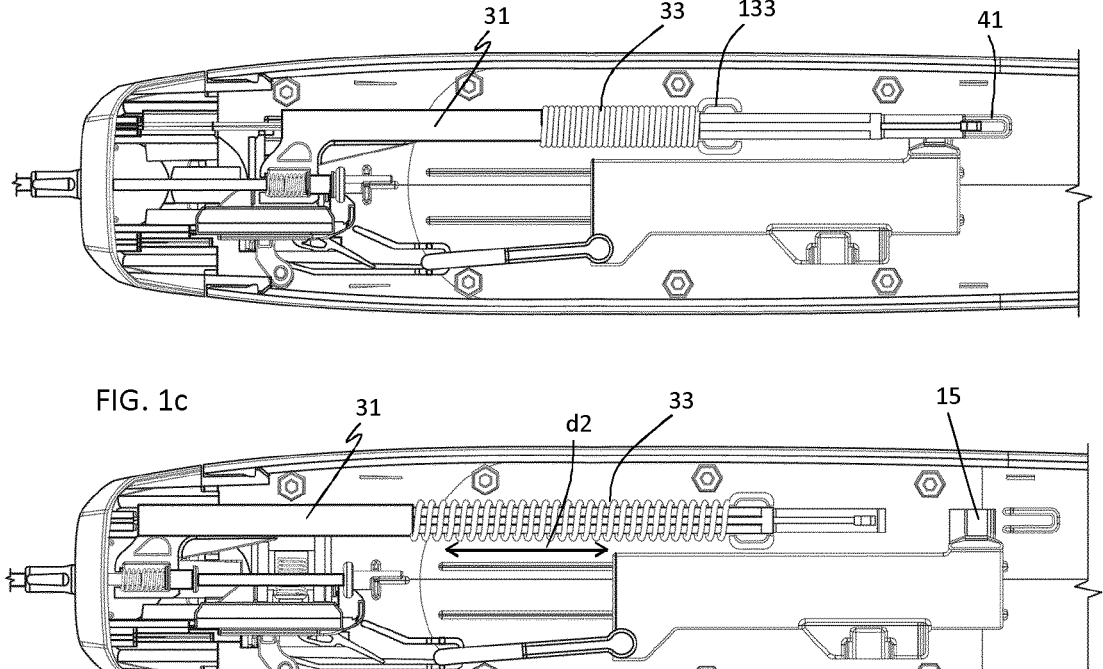

According to the invention the biopsy arrangement 1 further comprises an activator 11 which is arranged in the biopsy arrangement 1 such that it can be moved within the biopsy arrangement. Said activator 11 comprises a first activating part 13 which is configured to control a needle locking device 21 provided in the biopsy arrangement 1 to lock or not lock the inner needle part 5 and the outer needle part 7 to each other. The activator comprises also a second activating part 15 which is configured to control a needle translation device 31 provided in the biopsy arrangement 1 to change a position of the inner 5 and outer needle parts 7 in relation to each other. Said needle translation device 31 is connected to at least one of the inner or outer needle parts 5, 7. A movement of the activator 11 within the biopsy arrangement 1 will affect a position of both the first and the second activating parts 13, 15 whereby both the needle locking device 21 and the needle translation device 31 can be controlled by only moving the activator 11. In FIG. 1*a* the first activating part 13 is provided in a position such that it controls the needle locking device 21 to lock the inner and outer needle parts 5, 7 together. In FIG. 1*b* the actuator 11 has been moved a first distance d1 whereby the first activating part 13 is releasing the needle locking device 21 such that the needle locking device 21 is not locking the inner and outer needle parts 5, 7 to each other anymore. When the actuator 11 has been moved the first distance d1 the second activating part 15 will reach an activator engaging part 34 of the needle translation device 31 (seen in FIG. 2). When the activator 11 is moved further the needle translation device 31 is hereby also moved. In FIG. 1*c* the activator 11 has been moved a second distance d2, all the way back such that the needle translation device 31 reaches a release device 41 which will be further described below. Hereby the inner and outer needle parts 5, 7 have been moved in relation to each other by the needle translation device 31. In FIG. 1*d* the needle translation device 31 has been released from the activator 11 by the release device 41 which will be further described below. A resilient element 33 which was loaded during the retraction of the needle translation device 31 will then return the needle translation device 31 back to its original position and hereby the inner and outer needle parts 5, 7 are returned to initial position.

In this embodiment of the invention the needle translation device 31 comprises an outer needle connection member 35 connected to the outer needle part 7, whereby a translation of the needle translation device 31 is transferred to a translation of the outer needle part 7. However in another embodiment of the invention the needle translation device 31 comprises instead an inner needle connection member which is connected to the inner needle part 5, whereby a translation of the needle translation device 31 is transferred to a translation of the inner needle part 5.

The needle locking device 21 can be provided in at least a first needle locking device state and a second needle locking device state, where the needle locking device 21 in said first needle locking device state is locking the inner needle part 5 and the outer needle part 7 to each other such that they cannot be moved in relation to each other and in said second needle locking device state the needle locking device 21 is not locking the inner needle part 5 and the outer needle part 7 to each other. The first activating part 13 of the activator 11 can affect the state of the needle locking device 21 by movement of the activator 11, i.e. by moving the activator 11 the needle locking device 21 can be controlled to lock or not lock the inner needle part 5 and the outer needle part 7 to each other. The locking device 21 can be designed in different ways but in this embodiment a rear end (opposite a sharp insertion end) of the inner needle part 5 comprises a sliding region 22 along which a rear end of the outer needle part 7 can slide. The locking device 21 comprises a blocking part 23 which can be positioned over the sliding region 22 and hereby prevent the outer needle part 7 from sliding over the sliding region 22.

In this embodiment of the invention the activator 11 is arranged within the biopsy arrangement 1 such that it can be moved linearly within the biopsy arrangement in order to control the at least two different functions, i.e. locking or unlocking the needle part to each other and moving the needle parts in relation to each other. Hereby, by just moving the activator 11 linearly these two different functions can be controlled. Hereby said activator 11 can easily be connected to a motor, for example via an activator moving device 53*a* as will be described below, such that the position of the activator 11 can be controlled by the motor. In another embodiment of the invention the movement of the activator 11 within the biopsy arrangement 1 needs not to be linear but can instead be a rotary movement. Such a rotary movement can of course also easily be controlled by a motor.

Figure 2:
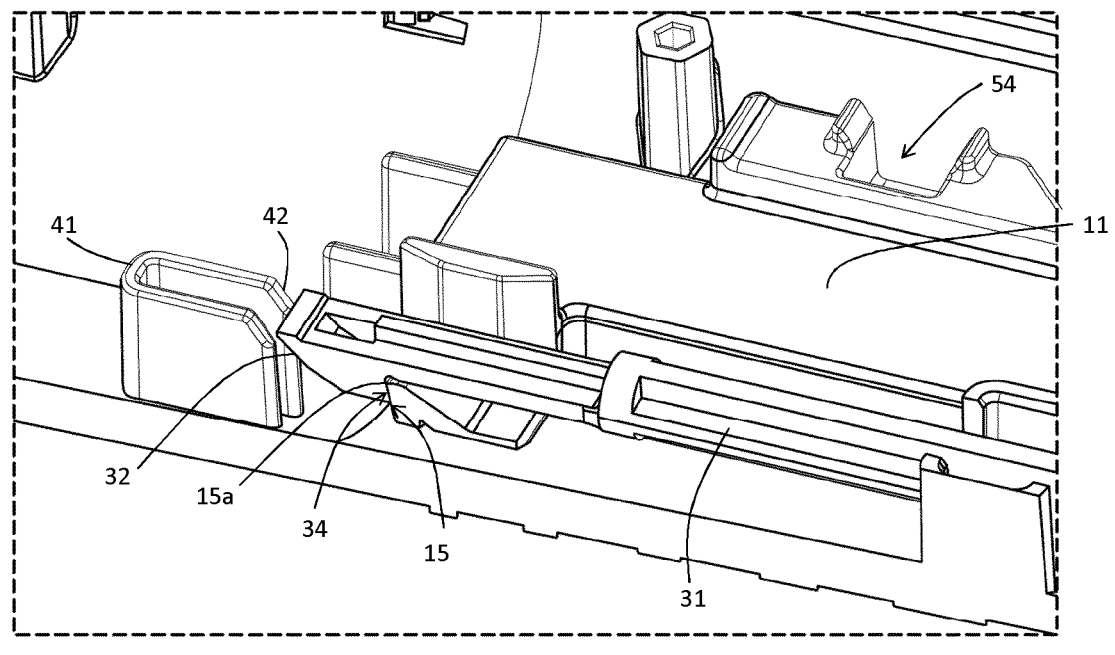
FIG. 2 is a perspective view of a part of an activator and a needle translation device according to one embodiment of the invention.

In the embodiment of the invention as shown in FIGS. 1-2 the biopsy arrangement 1 further comprises a release device 41 which is configured to release a connection between the second activating part 15 of the activator 11 and the needle translation device 31 when the activator 11 has been moved to a certain position. Hereby a movement of the activator 11 within the biopsy arrangement 1, possibly a linear movement as shown in FIGS. 1-2, can control at least three different functions comprising the control of the needle locking device 21 to lock or not lock the inner needle part 5 and the outer needle part 7 to each other, the control of the position of the inner and outer needle parts 5, 7 in relation to each other and the release of the connection between the second activating part 15 and the needle translation device 31. The release device 41 can be best seen in FIG. 2.

The needle translation device 31 comprises suitably as shown in FIGS. 1a-1d a resilient element 33 which will strive to return the inner or outer needle part 5, 7 if it has been moved, back to an original position. The release device 41 is positioned within the biopsy arrangement 1 such that it will release the connection between the second activating part 15 and the needle translation device 31 when the needle translation device 31 has been moved within the biopsy arrangement 1 by the second activating part 15 a second distance d2 and hereby the resilient element 33 has been loaded and will be released when the needle translation device 31 is released from the second activating part 15. The resilient element 33 can for example be a spring which is loaded when it compresses. A spring retaining device 133 can be provided within the biopsy arrangement 1 for holding the spring 33 and loading the spring 33 while the needle translation device 31 is moving. The release device 41 can be provided with a first inclined surface 42 which can counteract with a second inclined surface 32 of the needle translation device 31 such that when the needle translation device 31 is moved to such an extent that the first and second inclined surfaces 42, 32 are meeting the first inclined surfaces 42 will guide the second inclined surface 32 such that the needle translation device 31 is starting to move partly in a new direction. The actuator engaging part 34 of the needle translation device 31 will hereby slide over a shoulder 15a of the second activating part 15 such that the needle translation device 31 is released from the activator 11. The resilient element 33 will then force the needle translation device 31 back to an original position and hereby the outer and inner needle parts 5, 7 are also transferred back to an original position.

The at least two different functions, i.e. locking or unlocking the needle parts to each other and moving the needle parts in relation to each other can with this invention be performed by moving the activator in one single linear movement, i.e. in only one direction and not back and forth. In the embodiment as shown in FIGS. 1-7 the needle parts are first unlocked from each other and then the outer needle part is retracted by just moving the activator linearly in one direction. Furthermore, in this embodiment a third function is also controlled by the same linear movement of the activator in the same direction. This is the release of a connection between the second activating part 15 of the activator and the needle translation device.

Hereby, in some embodiments of the invention the inner needle part 5 can be kept in the same position during the whole sampling procedure, while the outer needle part 7 is first retracted by the activator acting on the needle translation device 31 and then forwarded by force from the resilient element 33. This is advantageous because the two needle parts can first be connected to each other and be positioned in an optimal sampling position and then the inner needle part is kept in this position during sampling and only the outer needle part is moving. Hereby sampling-precision can be improved.

Figures 6, 7:
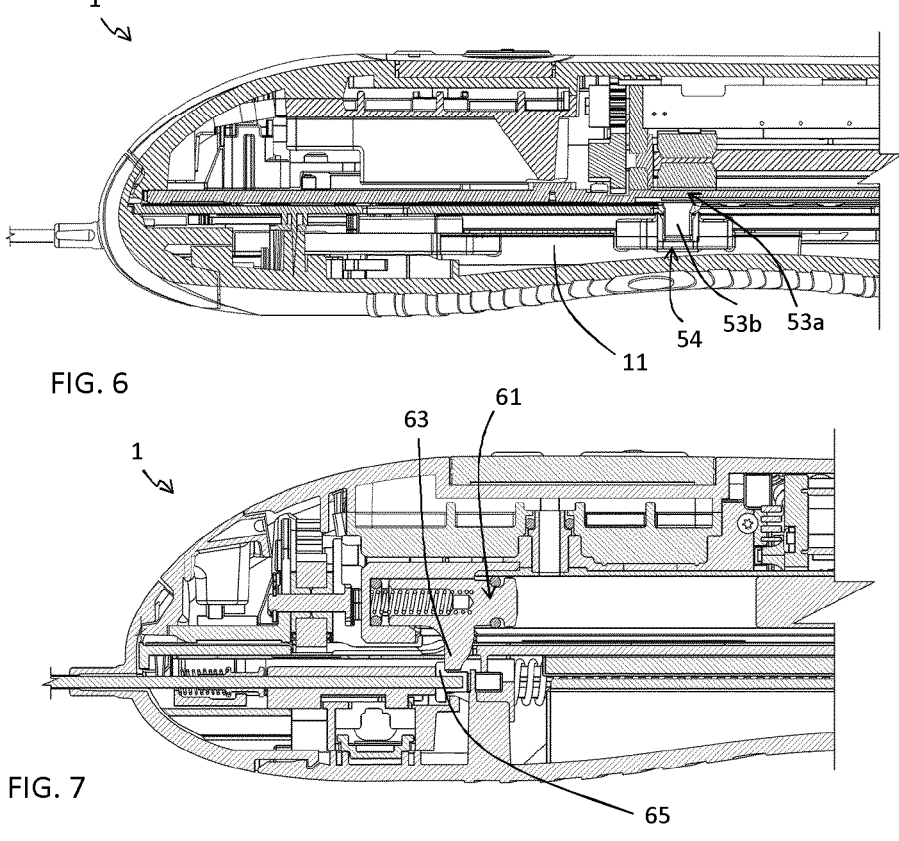
FIG. 6 is a cross section of a part of a biopsy arrangement according to one embodiment of the invention.
FIG. 7 is another cross section of a part of the same biopsy arrangement as shown in FIG. 6.

The biopsy arrangement comprises in some embodiments furthermore a pulsing device 61 which is configured to interact with the needle arrangement 3 such that reciprocating pulses of the pulsing device 61 can be transferred to the needle arrangement 3. The pulsing device 61 can be provided in a driver unit 51 of the biopsy arrangement 1 if the biopsy arrangement 1 is divided into two parts being a driver unit 51 and a single use probe 50 as described above. The driver unit 51 can be seen in FIG. 4 and the pulsing device 61 is best seen in FIG. 7. The pulsing device 61 comprises a needle interaction part 63 which is in contact with a pulse transferring part 65 of the needle arrangement 3. Hereby a reciprocating movement of the pulsing device 61 can be transferred to the needle arrangement 3 such that the needle arrangement can be pulsed during for example insertion of the needle arrangement 3 to a position where a sample should be taken. Hereby cutting through dense tissue and positioning of the needle is facilitated and improved thanks to the pulses and hereby the sampling procedure will be more convenient for the patient.

The driver unit 51 can be connected to a base unit (not shown). The base unit can provide power and possibly also vacuum and pressurized air to the driver unit 51. Alternatively the driver unit 51 can be connected directly to a power point without the need of a base unit in between. Power is needed both for moving the actuator 11 and for providing the pulses to the pulsing device 61.

The pulsing device 61 can be a piston arrangement. Such a piston arrangement comprises a piston arranged to reciprocate in a piston casing. This piston arrangement is driven by a movement generating source (not shown), e.g. weight accelerated by pressurized air generated by a compressor. Such a movement generating source can be provided either in the driver unit 51 or in a base unit to which the driver unit can be connected. In an alternative, the piston arrangement is driven by magnetic forces, hydraulic forces or spring-generated forces. In another alternative, the piston arrangement is driven by forces generated by an electric motor or a piezo-electric device. In EP 2323563, EP 3206587 and WO 2016/058845 the present applicant describes details of one type of pulsing device which can be used also in this invention.

The biopsy arrangement 1 comprises furthermore an activator moving device 53a comprising an activator engagement part 53b which is configured to engage with a translation position 54 of the activator 11. Hereby the activator 11 can be moved by moving the activator moving device 53a. The activator moving device 53a can for example be linearly moved by a connected motor.

As briefly discussed above said biopsy arrangement 1 can in some embodiments of the invention comprise a reusable driver unit 51 and a single use probe 50 which can be connected to each other during use of the biopsy arrangement. The single use probe 50 comprises said needle arrangement 3, said needle locking device 21, said needle translation device 31 and said activator 11 and said driver unit 51 comprises the activator moving device 53a. The driver unit 51 may further comprise the pulsing device 61.

The invention claimed is:

1. A biopsy arrangement for taking a biopsy in a human or animal tissue, said biopsy arrangement comprising:
   a biopsy arrangement housing;
   a needle arrangement comprising:
     an elongated inner needle part; and
     an elongated outer needle part, in which the outer needle part is a hollow member in which the inner needle part fits coaxially, wherein the outer needle part and the inner needle part can be provided in at least two different positions in relation to each other;
   a needle locking device;
   a needle translation device;
   an activator which is arranged in the biopsy arrangement housing, the activator configured to be moved within the biopsy arrangement housing, said activator comprising:

a first activating part which is configured to control the needle locking device provided in the biopsy arrangement housing to lock or not lock the inner needle part and the outer needle part to each other, the needle locking device is configured to move between at least a first needle locking device state and a second needle locking device state, wherein the needle locking device in said first needle locking device state is locking the inner needle part and the outer needle part to each other such that the inner needle part and the outer needle part cannot be moved in relation to each other and in said second needle locking device state, the needle locking device is not locking the inner needle part and the outer needle part to each other, whereby the first activating part is configured to move the needle locking device to one of the first needle locking device state or the second needle locking device state by movement of the activator; and a second activating part which is configured to control the needle translation device via an activator engagement part of the needle translation device to change positions of the inner needle part and the outer needle part in relation to each other, said needle translation device being connected to at least one of the inner needle part or the outer needle part, wherein the needle translation device comprises a resilient element configured to return the inner needle part or the outer needle part to an original position from a moved position, wherein the activator and the biopsy arrangement housing are configured such that movement of the activator within the biopsy arrangement housing affects positions of both the first activating part and the second activating part to control the needle locking device and the needle translation device; and a release device configured to release a connection between the second activating part of the activator and the needle translation device when the activator has been moved to a certain position, the release device is positioned within the biopsy arrangement housing such that the release device will release the connection between the second activating part and the needle translation device when the needle translation device has been moved within the biopsy arrangement housing by the second activating part a certain distance and hereby the resilient element has been loaded and will be released when the needle translation device is released from the second activating part, wherein the activator, via movement within the biopsy arrangement housing, is configured to control at least three different functions, including:

control the needle locking device to lock or not lock the inner needle part and the outer needle part to each other, control positions of the inner needle part and the outer needle part in relation to each other, and control release of the connection between the second activating part and the needle translation device, and wherein the activator is configured to be moved linearly in one direction in order to control the at least three different functions;

wherein the activator is configured to be moved linearly in the one direction in order to control the at least three different functions by a same linear movement of the activator in the one direction.

2. The biopsy arrangement according to claim 1, wherein said inner needle part comprises a sample receiving recess along a part of a length of the inner needle part, wherein said outer needle part can be provided in at least a first outer needle part position where the outer needle part is covering the sample receiving recess and a second outer needle position where the outer needle part is retracted and is not covering the sample receiving recess which is open for receiving a sample.

3. The biopsy arrangement according to claim 1, wherein the needle translation device comprises an outer needle connection member connected to the outer needle part, whereby a translation of the needle translation device is transferred to a translation of the outer needle part.

4. The biopsy arrangement according claim 1, whereby said activator is configured such that the activator can be connected to a motor such that a position of the activator can be controlled by the motor.

5. The biopsy arrangement according to claim 1, further comprising a pulsing device which is configured to interact with the needle arrangement such that reciprocating pulses of the pulsing device are transferred to the needle arrangement.

6. The biopsy arrangement according to claim 1, further comprising an activator moving device configured to engage the activator and transfer a movement to the activator.

7. The biopsy arrangement according to claim 1, comprising:

a single use probe, wherein said single use probe comprises:

said needle arrangement;

said needle locking device;

said needle translation device; and said activator; and a reusable driver unit, wherein said driver unit comprises:

an activator moving device configured to engage the activator and transfer a movement to the activator.

8. The biopsy arrangement according to claim 7, wherein the reusable driver unit further comprises a pulsing device.

9. The biopsy arrangement according to claim 5, further comprising an activator moving device configured to engage the activator and transfer a movement to the activator.

\* \* \* \* \*